United States Patent [19]

Lee

[11] 4,408,076

[45] Oct. 4, 1983

[54] PHENOXY UNSATURATED CARBOXYLIC ACID ESTERS AND DERIVATIVES

[75] Inventor: Shy-Fuh Lee, Sunnyvale, Calif.

[73] Assignee: Zoecon Corporation, Palo Alto, Calif.

[21] Appl. No.: 299,413

[22] Filed: Sep. 4, 1981

Related U.S. Application Data

[63] Continuation-in-part of Ser. No. 270,938, Jun. 5, 1981, abandoned, and Ser. No. 196,795, Oct. 14, 1980, abandoned.

[51] Int. Cl.³ .............................................. C07C 43/205
[52] U.S. Cl. ................................ 568/325; 260/465 D; 260/544 D; 544/349; 546/157; 546/301; 549/427; 549/501; 560/64; 560/183; 564/169; 564/271; 568/25; 568/31; 71/105; 71/108; 71/118; 71/123; 71/124
[58] Field of Search .................... 568/325; 260/465 D; 560/64

[56] References Cited

U.S. PATENT DOCUMENTS

| 3,869,515 | 3/1975 | Traber et al. | 568/325 |
| 4,058,627 | 11/1977 | Karrer et al. | 424/341 |
| 4,061,683 | 12/1977 | Karrer | 424/341 |
| 4,123,556 | 10/1978 | Karrer | 424/341 |
| 4,163,661 | 8/1979 | Jikihara et al. | 71/108 |

FOREIGN PATENT DOCUMENTS

| 2304962 | 8/1973 | Fed. Rep. of Germany. | |
| 2516515 | 10/1975 | Fed. Rep. of Germany. | |
| 2531643 | 3/1979 | Fed. Rep. of Germany. | |
| 55-20712 | 2/1980 | Japan | 568/325 |
| 1550574 | 8/1979 | United Kingdom. | |

*Primary Examiner*—Ethel G. Love
*Attorney, Agent, or Firm*—Darby & Darby

[57] ABSTRACT

3-Alkoxy-4-substituted-phenoxy-2,3-unsaturated acid esters and derivatives thereof and the use thereof for the control of weeds.

5 Claims, No Drawings

PHENOXY UNSATURATED CARBOXYLIC ACID ESTERS AND DERIVATIVES

This is a continuation-in-part of Ser. No. 270,938, filed June 5, 1981 and Ser. No. 196,795, filed Oct. 14, 1980, each now abandoned, the entire disclosures of which are incorporated herein by reference.

This invention relates to 3-alkoxy-4-substituted-phenoxy-2,3-unsaturated acid esters, derivatives thereof, and the use of said acid esters and derivatives for the control of weeds.

The novel 3-alkoxy-4- substituted-phenoxy-2,3-unsaturated acids, esters and derivatives thereof of the present invention are represented by the following formulas A′, B′, C′, and D′:

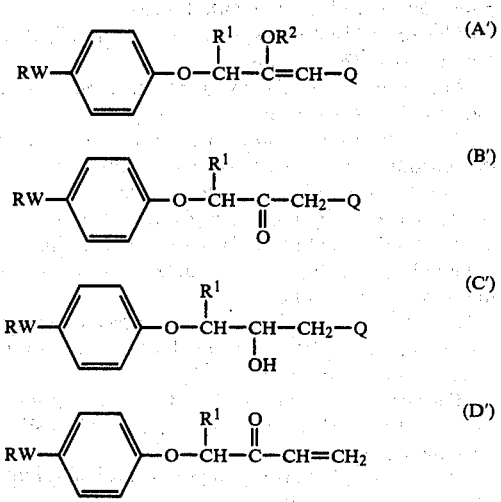

wherein,

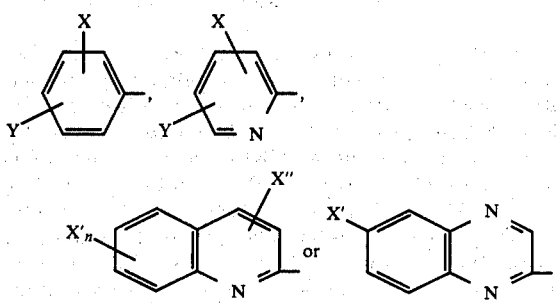

W is O, S, NH or $CH_2$;

each of X and Y is independently selected from hydrogen, bromo, chloro, fluoro, lower alkyl, lower alkoxy, lower alkoxycarbonyl, nitro, cyano, trifluoromethyl, chlorodifluoromethyl, fluoromethyl, chloromethyl, difluoromethoxy;

n is 1 or 2;

each of X′ and X″ is independently selected from hydrogen, fluoro, chloro, bromo, iodo, trifluoromethyl, methoxy or nitro, provided that both X′ and X″ cannot be trifluoromethyl, methoxy or nitro;

$R^1$ is hydrogen or lower alkyl;

$R^2$ is lower alkyl;

Q is

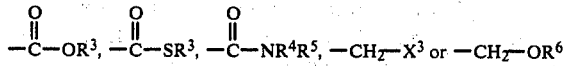

in which, $R^3$ is hydrogen, lower alkyl, lower haloalkyl, lower cyanoalkyl, lower alkenyl, lower haloalkenyl, lower alkynyl, lower alkoxyalkyl, lower dialkylaminoalkyl, lower alkylthioalkyl, lower alkylsulfinyalkyl, lower alkylsulfonylalkyl, tetrahphofuranylmethyl, tetrahydropyranylmethyl, benzyl, halobenzyl, lower alkylbenzyl, lower alkoxybenzyl, phenyl, halophenyl, lower alkoxyphenyl, lower alkylphenyl, cycloalkyl,cycloalkalkyl, N- alkylideneamino, sodium, potassium, magnesium or calcium;

each of $R^4$ and $R^5$ is independently selected from hydrogen, lower alkyl, lower hydroxyalkyl, lower alkoxyalkyl or lower alkylsulfonyl;

$X^3$ is bromo, chloro, fluoro or iodo; and $R^6$ is hydrogen or acyl.

In the description and claims hereinafter, each of R—$R^6$, n, Q, W, X, X′, X″, $X^3$ and Y is as defined above, unless otherwise specified.

The compounds of formula (A′) wherein Q is

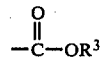

can be produced by the reaction of a phenol of formula (I).

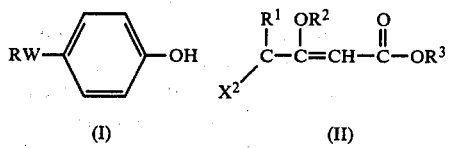

with a 4-halo compound of formula (II) in the presence of a base such as alkali metal hydroxide or alkali metal carbonate. The reaction is generally conducted at about room temperature to reflux temperature in an organic solvent such as dimethylformamide (DMF), acetone, tetrahydrofuran (THF), dimethylacetamide (DMA), dimethylsulfoxide (DMSO), or the like using about equimolar amounts of base, a phenol of formula (I) and a 4-halo compound of formula (II). $X^2$ represents bromo, chloro or iodo.

The thio compounds of formula (A′) can be prepared starting with an acid of formula (A′) which is converted into the acid halide and then reacted with a mercaptan. Alternatively, a phenol of formula (I) is reacted with a 4-halo thiolester of the general formula (II) above in the presence of base.

An amide of formula (A′) can be prepared by the reaction of an acid halide of an acid of formula (A′) with the appropriate amine.

An alcohol of formula (A′) wherein Q is —$CH_2$—$OR^6$ can be prepared by reduction of an acid or ester of formula (A′) using, for example, lithium borohydride or lithium aluminumhydride in ether or THF at a low temperature. Esters of an alcohol of formula (A′) can be prepared by the reaction of an acyl halide or acyl anhydride in pyridine at about room temperature or lower.

A halide of the present invention of formula (A′) wherein Q is —$CH_2$—$X^3$ can be prepared by reaction of an alcohol of formula (A') wherein Q is —CH$_2$—OH with phosphorus tribromide, phosphorus trichloride, or triphenylphosphine dihalide in acetonitrile. In another embodiment of the present invention, there is provided 3-oxo derivatives of formula (B') which can be derived from the novel compounds of formula (A'). The compounds of formula (B') are useful for the control of weeds.

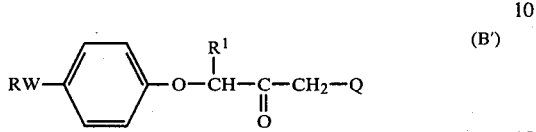

A compound of formula (B') can be prepared by the reaction of a 3-alkoxy compound of formula (A') such as a 3-methoxy compounds of formula (A') with an acid such as dilute perchloric acid or acetic acid in an organic solvent such as methylenedichloride, tetrachloride or THF. The reaction is usually conducted at about room temperature or lower. In another embodiment of the present invention, there is provided compounds of formula (C') which can be prepared by selective reduction of a compound of formula (B') using sodium borohydride in alcohol at low temperature.

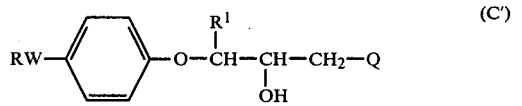

The alcohols of formula (C') and carboxylic esters thereof are useful for the control of weeds.

In another embodiment of the present invention, there is provided compounds of formula (D') which are useful for the control of weeds.

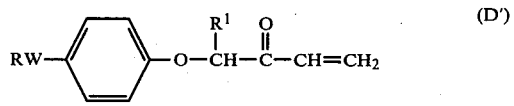

The compounds of formula (D') can be prepared by treating an alcohol of formula wherein Q is —CH$_2$—OH with perchloric acid.

Carboxylic esters of formula (B') wherein Q is

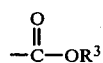

can be prepared by the following outlined method also:

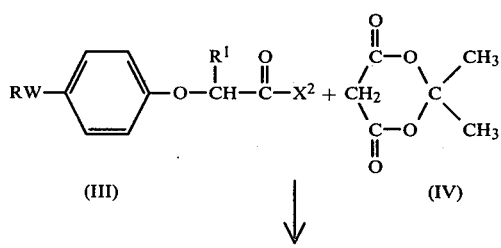

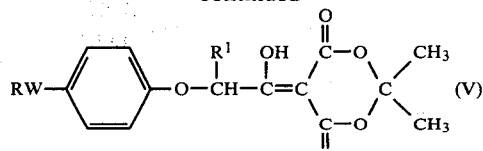

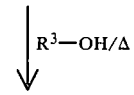

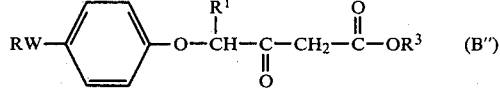

The following terms have the meaning indicated as used herein and the appended claims.

The term "lower alkyl" refers to an alkyl group of one to six carbon atoms.

The term "lower alkoxy" refers to an alkoxy group of one to six carbon atoms.

The term "lower alkoxycarbonyl" refers to an alkoxycarbonyl group of two to six carbon atoms.

The term "acyl" refers to a carboxylic acyl group such as lower aliphatic acyl group of one to six carbon atoms or aryl acyl group of six to twelve carbon atoms. Typical acyl groups include acetyl, benzoyl, p-chlorobenzoyl, and the like.

The term "lower alkenyl" refers to an alkenyl group of two to six carbon atoms with mono-unsaturation such as allyl and n-but-2-enyl.

The term "lower alkynyl" refers to an alkynyl group of two to six carbon atoms with monounsaturation such as propargyl.

The term "cycloalkyl" refers to a cycloalkyl group of three to six carbon atoms.

The term "cycloalkyl" refers to a cycloalkalkyl group of four to seven carbon atoms.

The term "halo" refers to a bromo, chloro or fluoro group.

The compounds of formula A', B', C', D' are useful for the control of weeds using pre- and/or post-emergent treatments. The compounds can be applied in the form of dusts, granules, solutions, emulsions, wettable powders and suspensions. Application of a compound of the present invention is made according to conventional procedure using from about one-half or less to ten pounds per acre. The application of a compound of the present invention to the "locus" of the weeds includes application to the seeds, the plant (weed) or parts of the plant, or the soil. Methods of preparing herbicidal formulations which can be used with a compound of the present invention are described in the literature along with suitable liquid and solid carrier materials such as in U.S. Pat. Nos. 4,192,669 and 4,163,661 which are incorporated herein by reference. While some of the compounds of the present invention have activity on broad leaf plants, the compounds, in general, demonstrate a higher level of herbicidal activity on the grass weeds. The optimum usage of a compound of the present invention is readily determinable by one of ordinary skill in the art using routine testing such as greenhouse testing and small plot testing.

The term "herbicide", as used herein, refers to an active ingredient which modifies the growth of plants because of phytotoxic or plant growth regulating properties so as to retard the growth of the plant or damage the plant sufficiently to kill it.

The compounds of the present invention demonstrate selective activity as herbicides against grass weeds. Crops such as cotton, sugar beet, soybeans and squash show excellent tolerance. The compounds of the present invention, in general, show higher level of herbicidal activity when the postemergent method of application is used. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

The compounds of the present invention, in view of their broadspectrum grass weed herbicidal activity, can be advantageously combined with broadleaf weed herbicides for broadspectrum postermergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The compounds of the present invention are useful for application to sugarcane in order to increase the sucrose content of the sugarcane.

The following examples are provided to illustrate the practice of the present invention. Temperature is given in degrees centigrade. All parts are by weight unless otherwise indicated. RT means room temperature.

EXAMPLE 1

A mixture of 4-(2-chloro-4-trifluoromethylphenoxy) phenol (1.16 g), ethyl 4-bromo-3-methoxy-2-pentenoate (1.74 g) and potassium carbonate (0.73 g) in DMF (5 ml.) is heated at about 130° for 2 hours. Thereafter, DMF is removed. The residue is filtered and washed with methylene dichloride. The filtrate is washed, dried and evaporated to dryness. The oily residue is subjected to prep. thin layer chromatography using 20% ethylacetate/hexane to yield the ethyl ester of 4-[4-(2-chloro-4-trifluoromethylphenoxy) phenoxy]-3-methoxy-2-pentenoic acid, MS m/e 444 (M+).

EXAMPLE 2

A mixture of 4-(2-chloro-4-trifluoromethylphenoxy) phenol (6.9 mmol.), methyl 4-bromo-3-methoxy-2-pentenoate (8.9 mmol.) and potassium carbonate (1.5 equis.) in acetone (15 ml.) is refluxed for 48 hours. After filtration, the filtrate was concentrated and the residue chromatographed on silica gel using 20% ethylacetate/hexane to give the methyl ester of 4-[4-(2-chloro-4-trifluoromethylphenoxy)phenoxy]-3-methoxy-2-pentenoic acid.

Some compounds of formula A' which are prepared according to the procedure of the foregoing examples are as follows (Table I and II).

TABLE I $$Y-\underset{X}{\bigcirc}-O-\bigcirc-O-CH-\underset{R^1}{C}=CH-\underset{}{C}-OR^3$$
(with $OR^2$ on the central carbon)

| X | Y | R¹ | R² | R³ |
|---|---|----|----|----|
| H | CF₃ | Me | Me | Me |
| H | CF₃ | Et | Me | Me |
| Cl | CF₃ | Et | Me | Me |
| Cl | CF₃ | Me | Et | Me |
| H | OCF₃ | Me | Me | Me |
| Cl | OCF₃ | Me | Me | Me |
| Cl | Cl | Me | Me | Et |
| NO₂ | CF₃ | Me | Me | Me |
| H | Br | Me | Me | Et |
| Me | OMe | Me | Me | Me |

TABLE II (pyridyloxy analog)

| X | Y | R¹ | R² | R³ |
|---|---|----|----|----|
| Cl | Cl | Me | Me | Me |
| H | CF₃ | Me | Me | Me |
| Cl | CF₃ | Me | Me | Me |
| H | CHF₂ | Me | Me | Me |
| H | CClF₂ | Me | Me | Me |
| Me | CF₃ | Et | Me | Et |
| F | CF₃ | Me | Me | Me |
| H | Br | Me | Me | Me |
| Cl | Cl | Me | Et | Et |
| Cl | Cl | Et | Et | Et |

EXAMPLE 3

A mixture of the methyl ester of 4-[4-(2-chloro-4-trifluoromethylphenoxy) phenoxy]-3-methoxy-2-pentenoic acid (0.5 g), 35% aqueous perchloric acid (5 ml.) and methylene dichloride (5 ml.) is stirred at RT for 4 days. Then the solution is extracted with methylene dichloride. The combined extracts are washed, dried and evaporated. The residue is purified by prep. thin layer chromatography using 20% ethyl acetate/hexane to yield methyl 4-[4-(2-chloro-4-trifluoromethylphenoxy) phenoxy]-3- oxopentanoate.

The product of Example 1 is treated with aqueous perchloric acid as above to yield ethyl 4-[4-(2-chloro-4-trifluoromethylphenoxy) phenoxy]-3-oxopentanoate, MS m/e 430 (M+).

By use of the foregoing procedure, each of the compounds of Tables I and II are converted into the corresponding 3-oxocompound of formula (F) such as methyl 4-[4-(4-trifluoromethylphenoxy)phenoxy]-3-oxopentanoate, methyl 4-[4-(4-trifluoromethoxyphenoxy)phenoxy]-3-oxopentanoate, ethyl 4-[4-(2,4-dichlorophenoxy)phenoxy]-3-oxopentanoate, MS m/e 396 (M+), methyl 4-[4-(4-dichlorophenoxy)phenoxy]-3-oxopentanoate, methyl 4-[4-(3,5-dichloropyridyloxy)-phenoxy]-3-oxopentanoate and methyl 4-[4-(5-trifluoromethylpyridyloxy)phenoxy]-3-oxopentanoate.

EXAMPLE 4

A mixture of 4-(2-nitro-4-trifluoromethylphenoxy) phenol (9.36 mm)., ethyl 4-bromo-3-methoxy-2-pentenoate (12 mm.) and K₂CO₃ (14 mm.) in acetone (20 ml.) is refluxed for 24 hours. After filtration, the filtrate is concentrated and the oily residue chromatographed on silica gel to yield ethyl 4-[4-(2-nitro-4-trifluoromethylphenoxy)phenoxy]-3-methoxy-2-pentenoate.

A solution of the above ethyl ester in 35% perchloric acid and water is stirred at RT for 3 days and then worked up to give ethyl 4-[4-(2-nitro-4-trifluoromethylphenoxy) phenoxy-3-oxopentanoate.

EXAMPLE 5

To a mixture of lithium aluminum hydride (200 mg) and anhydrous ether (5 ml.) is added dropwise at 0°, a mixture of ethyl 4[4-(2-chloro-4-trifluoromethylphenoxy)phenoxy]-3-methoxy-2-pentenoate (400 mg) and ether (5 ml.). After addition is complete, the mixture is stirred for about minutes. Wet ether and water is added to destroy excess hydride. Filtration and evaporation of filtrate gives 4-[4-(2-chloro-4-trifluoromethylphenoxy)phenoxy]-3-methoxy-2-penten-1-ol.

EXAMPLE 6

A mixture of ethyl 4-[4-(2-chloro-4-trifluoromethylphenoxy)phenoxy]-3-methoxy-2-pentenoate (10 mmol), ethanol (20 ml.) and 1 N Na OH (20 ml.) is prepared and then heated at reflux for a few hours to complete the reaction. Removal of solvent gives the sodium salt of 4-[4-(2-chloro-4-trifluoromethylphenoxy)phenoxy]-3-methoxy-2-pentenoic acid. The free acid is obtained by acidification of the salt using dilute $H_2SO_4$, and extraction with methylene dichloride and evaporation. Other acid salts can be prepared by titrating the free acid with an organic solution of the base, e.g., methanolic solution of potassium methoxide and the like.

EXAMPLE 7

Thionyl chloride (20 ml.) is added to 4-[4-(2-chloro-4-trifluoromethylphenoxy)phenoxy]-3-methoxy-2-pentenoic acid (10 mm.) in anhydrous ether (10 ml.). The mixture is refluxed for a few hours. Then, ether and excess thionyl chloride is removed by vacuum to yield 4-[4-(2-chloro-4-trifluoromethylphenoxy)phenoxy]-3-methoxy-2-pentenoyl chloride.

EXAMPLE 8

To a mixture of 4-[4-(2-chloro-4-trifluoromethylphenoxy) phenoxy]-3-methoxy-2-pentenoyl chloride (10 mm.) and ether (10 ml.) is added methyl mercaptan (12 mm.) and pyridine (1 ml.) at about −20°. The mixture is stirred for about 30 minutes and then allowed to rise to about 0° and stand for about 2 hours. The mixture is then diluted with ether and water and the ether phase separated, washed, dried and solvent removed to give the methylthiol ester of 4-[4-(2-chloro-4-trifluoromethylphenoxy) phenoxy]-3-methoxy-2-pentenoic acid.

EXAMPLE 9

A mixture of 4-[4-(2-chloro-4-trifluoromethylphenoxy) phenoxy) phenoxy]-3-methoxy-2-pentenoyl chloride (15 mm) and THF (15 ml.), at 0°, is prepared and then slight excess of methylamine introduced. The reaction mixture is allowed to stand under nitrogen for about one hour. Then the reaction is allowed to rise to RT and solvent removed. The residue is taken up in methylene dichloride, washed, dried and solvent removed under vacuum to yield N-methyl 4-[4-(2-chloro-4-trifluoromethylphenoxy) phenoxy]-3-methoxy-2-pentenamide.

EXAMPLE 10

A mixture of ethyl 3-oxopentanoate (20 g) and trimethylformate (5 eq.,94 ml.) in the presence of 6 g of Amberlyst-15 (trademark of Rohm & Haas Corp.) is stirred at RT overnight. After filtration, the filtrate is concentrated and then distilled to give ethyl 3-methoxy-2-pentenoate (19.5 g).

A mixture of the above ethyl ester, N-bromosuccinimide (26.3 g), benzoyl peroxide (0.3 g.) and carbon tetrachloride (100 ml.) is heated to reflux and irradiated with 150 watt flood lamp until substantially clear solution is obtained. Thereafter, the reaction is filtered and the filtrate then concentrated and distilled (78°/2 mm) to give ethyl 4-bromo-3-methoxy-2-pentenoate.

EXAMPLE 11

(A) Following the procedure of Example 1, 4-(2-nitro-4-trifluoromethylphenylamino) phenol is reacted with ethyl 4-bromo-3-methoxy-2-pentenoate to give ethyl 4-[4-(2-nitro-4-trifluoromethylphenylamino)phenoxy]-3-methoxy-2-pentenoate.

(B) Following the procedure of Example 3, the product of part (A) is treated with aqueous perchloric acid to give ethyl 4-[4-(2-nitro-4-trifluoromethylphenylamino)phenoxyl]-3 oxopentanoate, MS m/e 512 (M+).

In the same way, there is prepared methyl 4-[4-(2-nitro-4- chlorophenylamino)phenoxy]-3-methoxy-2-pentenoate and methyl 4-[4-(2-nitro-4-chlorophenylamino)phenoxy]-3-oxopentanoate starting with 4-(4-chloro-2-nitrophenylamino) phenol and methyl 4-bromo-3-methoxy-2-pentenoate.

EXAMPLE 12

A spray solution of water/acetone (1:1) and surfactant (1%) was prepared containing (1) the compound of Example 1 (Compound 1) and (2) the second compound of Example 3 (Compound 2) and sprayed (equivalent to 10 lb/acre) on seedlings of foxtail (Setaria viridis) and watergrass (Echinochlou crusgalli). Observation two weeks after spraying Compound 1 and 2 showed 100% herbicidal activity for each of test Compounds 1 and 2. Testing of Compounds 1 and 2 showed no injury to soybeans at 10 lb/acre.

Pre-emergent herbicidal activity of Compound 2 was tested on foxtail, watergrass, shattercane, and wild oats. The average activity was 86% for the four species.

EXAMPLE 13

To a slurry of $LiAlH_4$ (100 mg) in anhydrous ether (20 ml) is added dropwise at 0°, a solution of ethyl 4-[4-(4-trifluoromethylphenoxy)phenoxy]-3-methoxy-2-pentenoate (500 mg) in ether. After addition is complete, the reaction mixture is stirred for about 20 minutes. Excess of the hydride is decomposed using wet ether and water. Filtration and evaporation of filtrate gives the C-1 alcohol,4-[4-(4-trifluormethylphenoxy)phenoxy]-3-methoxy-2-penten-1-ol, MS m/e 440 (M+).

EXAMPLE 14

To a slurry of $LiAlH_4$ (200 mg) in anhydrous ether (15 ml) is added at 0° a solution of ethyl 4-[4-(4-trifluoromethylphenoxy)phenoxy]-3-oxopentanoate(400 mg) in ether (5 ml). After addition is complete, the reaction mixture is stirred at RT for about one hour. Excess of the hydride is decomposed using wet ether and water, the mixture is filtered and filtrate concentrated. The oily product is purified by prep. thin layer chromatography to give 4-[4-(4-trifluoromethylphenoxy)phenoxy]-pentane-1,3-diol, MS m/e 500 (M+).

EXAMPLE 15

To a solution of ethyl 4-[4-(2-nitro-4-chlorophenoxy)phenoxyy]-3-oxopentanoate (600 mg) in absolute ethanol (10 ml) is added at 0°, NaBH$_4$ (300 mg). After addition is complete, the reaction mixture is stirred for about 20 minutes. Then the solution is taken up in CH$_2$Cl$_2$, washed with brine, dried and evaporated to give ethyl 4-[4-(2-nitro-4chlorophenoxy)phenoxy]-3-hydroxypentanoate.

EXAMPLE 16

To a slurry of LiAlH$_4$ (400 mg) in anhydrous ether (20 ml) is added dropwise at 0°, a solution of ethyl 4-[4-(4-trifluoromethylphenoxy)phenoxy]-3-methoxy-2-pentenoate (1.2 g) in ether (10 ml). After addition is complete, the reaction mixture is stirred for about 10 minutes. Excess hydride is decomposed with wet ether and water. After filtration, the filtrate is concentrated to give the alcohol, 4-[4-(4-trifluoromethylphenoxy) phenoxy]-3-methoxy-2-penten-1-ol.

The alcohol (600 mg) is stirred with 5 ml of 35% HClO$_4$ in CH$_2$Cl$_2$ (5 ml) for about 20 minutes. The solution is then extracted with CH$_2$Cl$_2$ followed by washing, drying and evaporation. The product is then purified by prep. thin layer chromatography to give 4-[4-(4-trifluoromethylphenoxy)phenoxy]-3-oxo-1-pentene, MS m/e 336 (M+).

EXAMPLE 17

To a solution of ethyl 4-[4-(4trifluoromethylphenoxy)phenoxy]-3-oxopentanoate (450 mg) in ethanol (5 ml) is added NaBH$_4$ (150 mg) at 0°. The resulting mixture is then stirred at 0° for about 10 minutes. The mixture is diluted with CH$_2$Cl$_2$, washed with saturated NaCl solution, dried and evaporated to dryness to give ethyl 4-[4-(4-trifluoromethylphenoxy)phenoxy]-3-hydroxypentanoate, in quantitative yield, MS m/e 398 (M+).

EXAMPLE 18

The process of Example 17 is repeated using ethyl 4-[4-(2chloro-4trifluoromethylphenoxy)phenoxy]-3-oxopentanoate (400 mg) and NaBH$_4$ (100 mg) to give ethyl 4-[4-(2-chloro-4-trifluoromethylphenoxy)phenoxy]-3-hydroxypentanoate, MS m/e 432 (M+).

EXAMPLE 19

To a slurry solution of LiAlH$_4$ (200 mg) in anhydrous ether (5 ml) is added dropwise at 0°, a solution of ethyl 4-[4-(2-chloro-4-trifluoromethylphenoxy)phenoxy]-3-methoxy-2-pentenoate (400 mg) in anhydrous ether (5 ml). After addition is complete, the reaction mixture is stirred at 0° for about 10 minutes. Excess hydride is decomposed with wet ether and water. The mixture is filtered and filtrate washed, dried and evaporated to give 4-[4-(2-chloro-4-trifluoromethylphenoxy) phenoxy]-3-methoxy-2-penten-1-ol.

The foregoing alcohol (380 mg) is reacted with 35% HClO$_4$ (4 ml) in CH$_2$Cl$_2$ (4 ml) at RT for 24 hours. The mixture is then extracted with CH$_2$Cl$_2$ and the combined extracts washed, dried and concentrated to dryness. The product is purified by prep. thin layer chromatography to give 4-[4-(2-chloro-4trifluoromethylphenoxy)phenoxy]-3-oxo-1-pentene, MS m/e 396 (M+).

EXAMPLE 20

A solution of 2-[4-(4-trifluoromethylphenoxy)phenoxy]-propionyl chloride (1.5 g) and methylene chloride (5 ml) is added dropwise at 0° to a solution of 2,2-dimethyl-1,3-dioxane-4,6-dione (680 mg) in methylene chloride (20 ml) containing pyridine (0.7 ml). The resulting mixture is stirred at RT for 2 hours. The reaction mixture is then poured into water, acidified with dilute HCl and extracted with methylene chloride. The combined extracts are washed with brine, dried and evaporated to give 2-[4-(4trifluoromethylphenoxy)phenoxy]-propionyl meldrum acid, an oil.

The above meldrum acid is treated with n-butanol (20 ml) at 120° for about 4 hours. After aqueous workup, the oily concentrate is purified by prep. thin layer chromatography on silica gel to give n-butyl 4-[4-(4-trifluoromethylphenoxy) phenoxy]-3-oxopentanoate, MS m/e 424 (M+).

EXAMPLE 21

A mixture of 2-nitro-3-trifluoromethyl-4'-hydroxydiphenylamine (1 g), ethyl 4-bromo-3-methoxy-2-pentenoate (990 mg) and potassium carbonate (694 mg) in acetone (10 ml) is refluxed for 24 hours. After filtration and concentration, the crude product is purified by prep. thin layer chromatography on silica gel to give ethyl 4-[4-(2-nitro-4-trifluoromethylanilino)phenoxy]-3-methoxy-2-pentenoate which is treated with 35% HClO$_4$ in methylene chloride to give ethyl 4-[4-(2-nitro 4-trifluoromethylanilino)phenoxy]-3-oxopentanoate, MS m/e 440 (M+).

EXAMPLE 22

Post-emergence activity on the grasses (GR) greenfoxtail, watergrass, shattercane and wild oats was tested for the compound of Examples 13, 14, 17, 18, 20 and 21 (compounds No. 3, 4, 5, 6, 7 and 8, respectively) and on the broadleafs (BL) annual morningglory, sesboria, soybean and velvet leaf by spraying at rate equivalent to 10 lb/acre. The average score is given in percent control.

| Compound No. | GR | BL |
| --- | --- | --- |
| 3 | 100 | 14 |
| 4 | 96 | 8 |
| 5 | 100 | 11 |
| 6 | 100 | 3 |
| 7 | 100 | 7 |
| 8 | 100 | 0 |

EXAMPLE 23

An emulsifiable concentrate was prepared having the following composition (components in percent by weight).

| (VI) | Compound B | 27.78 |
| --- | --- | --- |
| | Igepol CO-530 | 2.67 |
| | Tween 21 | 2.67 |
| | Tween 81 | 2.67 |
| | Corn oil | 64.21 |

Compound B is ethyl 4-[4-(4-trifluoromethylphenoxy)phenoxy]-3-oxopentanoate (90% purity). Tween 21 is non-ionic surfactant, polyoxyethylene sorbitan monolaurate and Tween 81 is polyoxyethylene sorbitan monooleate. Tween is a trademark of ICI Americas. Igepal CO-530 is a non-ionic surfactant [nonylphenoxypoly(ethyleneoxy)ethanol] of GAF, Inc.

|      |              |      |
|------|--------------|------|
| (VII)| Compound C   | 29.3 |
|      | Toximol S    | 6.4  |
|      | Atlox 8916 TF| 1.6  |
|      | Tenneco 500-100 | 62.7 |

Compound C is ethyl 4-[4-(4-trifluoromethylphenoxy) phenoxy]-3-hydroxypentanoate (90% purity).

A spray solution was prepared using 30 parts of concentrate VII, 950 parts of water and 28 parts of non-phytotoxic crop oil and applied to young Johnson grass at the rate of 1.0 lb. per acre. The test plots were observed after two weeks. The application gave 100% control of the Johnson grass.

|       |              |      |
|-------|--------------|------|
| (VIII)| Compound B   | 27.8 |
|       | Toximol R    | 3.0  |
|       | Toximol S    | 9.0  |
|       | Tenneco 500-100 | 60.2 |

Concentrate VIII was diluted in water and applied at the rate of 2.0 lb. per acre to test specimens, in a greenhouse, of watergrass, green foxtail, shattercane, blue panicum, tallfescue, spangletop, annual ryegrass, downy brome, wild oats, crabgrass, milo, corn, probred wheat and barley. The average herbicidal activity of two or more evaluations of each of the foregoing grass species was 80% or greater.

Toximol R and S are surfactants of the Stepan Chemical Corporation, Illinios. Atlox 8916F in a surfactant of ICI Americas, Delaware. Tenneco 500-100 is an aromatic solvent of the Tenneco Corporation.

EXAMPLE 24

Flowable formulations were prepared having the following compositions, percent by weight.

|      |     |                |       |
|------|-----|----------------|-------|
| (XI) | (A) | Compound B     | 3.00  |
|      |     | Toximol 360A   | 3.00  |
|      |     | Sun 7N (oil)   | 30.00 |
|      | (B) | Water          | 60.85 |
|      |     | Gelvatol 20/30 | 3.00  |
|      |     | Kelzan         | 0.15  |

Premix (A) was dispersed in high speed blender for about one minute and then Premix (B) was poured into Premix (A) while stirring at high speed. After addition of Premix (B) stirring was continued about 5 minutes.

|     |     |                |       |
|-----|-----|----------------|-------|
| (X) | (A) | Compound C     | 3.00  |
|     |     | Toximol 360A   | 3.00  |
|     |     | Sun 7N         | 30.00 |
|     | (B) | Water          | 60.85 |
|     |     | Gelvatol 20/30 | 3.00  |
|     |     | Darvan No. 1   | 0.15  |

Premix (A) and (B) were combined as described for flowable IX above. Concentration of active ingredient 2.7%.

Sun 7N is a non-phytotoxic oil of the Sun Chemical Company. Gelvatol 20/30 is a polyvinyl alcohol, molecular weight about 10000 of the Monsanto COmpany. Kelzan is a thickener agent (xanthum gum). Darvan No. 1 is a dispersant of the RT Vanderbilt Company.

EXAMPLE 25

The compound, 2-[4-(4-trifluoromethylphenoxy)-phenoxy]propionyl meldrum acid (V; W is oxygen, R is 4-trifluoromethylphenyl, and $R^1$ is methyl) is reacted with the alcohol $R^3$-OH using the procedure of Example 20 to prepare the respective ester under Table III.

TABLE III

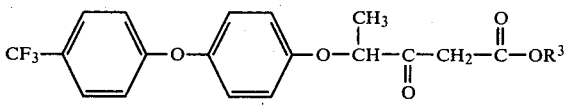

| $R^3$ |
|---|
| $-CH_2-CN$ |
| $-CH_2-CH=CH_2$ |
| $-CH_2-CH=C\,Cl_2$ |
| $-CH_2-C\equiv CH$ |
| $-CH_2-CH_2-O-CH_3$ |

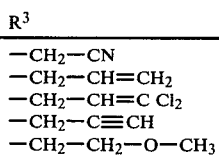

$-CH_2-CH_2-Cl$

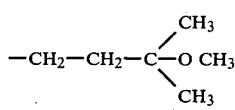

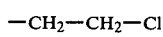

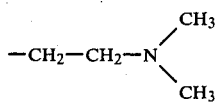

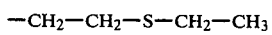

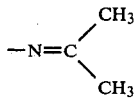

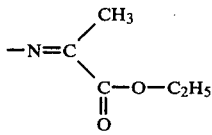

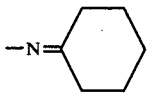

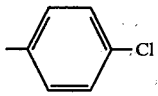

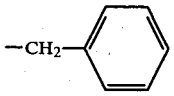

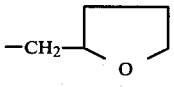

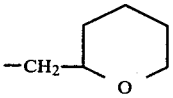

TABLE III-continued

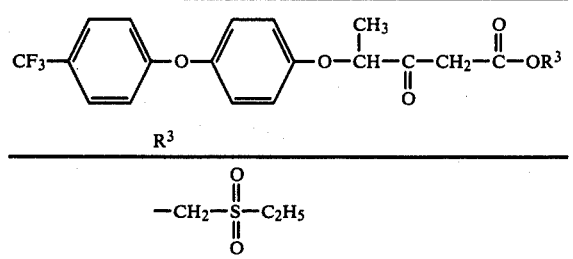

R³

$$-CH_2-\overset{O}{\underset{O}{\overset{\|}{S}}}-C_2H_5$$

EXAMPLE 26

Following the procedure of Example 17, each of the 3-oxo esters under Table III is reduced using sodium borohydride to yield the respective 3-hydroxy esters of the following formula:

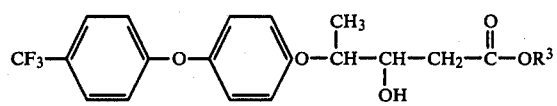

EXAMPLE 27

Ethyl 4-[4-(4-trifluoromethylphenoxy)phenoxy]-3-hydroxypentanoate is reacted with 1.1 equivalent of acetyl chloride and 1.0 equivalent of pyridine in benzene to yield ethyl 4-[4-(4-trifluoromethylphenoxy)phenoxy]-3-acetoxypentanoate. Similarly, using n-propanoyl chloride and isopropanoyl chloride yield the respective 3-n-propanate and 3-isopropanoate.

Carbonates of the 3-hydroxy compounds of formula C' are prepared using the above procedure and 1.1 equivalents of, for example, ethyl chloroformate or methyl chloroformate. The 3-carbonates are useful herbicides for grass weeds also.

In the preparation of the 3-hydroxy compounds of formula C', in addition to reduction of the respective 3-oxo compound of formula B', the 3-hydroxy compounds such as the esters can be prepared by the following outlined method.

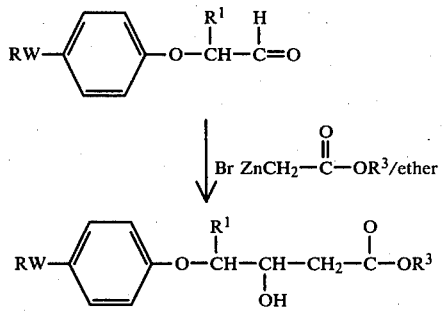

The compounds of the present invention include the isomeric forms and mixtures thereof. Thus, the invention includes the optically active isomers and racemic mixtures. Unless otherwise specified herein, the compounds described in the examples are racemic mixtures.

EXAMPLE 28

Each of the compounds, methyl 4-[4-(3,5-dickloropyridyloxy)phenoxy]-3-oxopentanoate and methyl 4-[4-(5-trifluoromethylpyridyloxy)phenoxy]-3-oxopentanoate is reacted with NaBH₄ by the procedure of Example 17 to yield methyl 4-[4-(3,5-dichloropyridyloxy)phenoxy]-3-hydroxypentanoate and methyl 4-[4-(5-trifluoromethylpyridyloxy)phenoxy]-3-hydroxypentanoate, respectively.

EXAMPLE 29

The process of Example 20 is repeated with the exception of using 2-[4-(6-chloro-2-quinolinyloxy)phenoxy]-propionyl chloride as the starting material in place of 2-[-(4-trifluoromethylphenoxy)phenoxy]-propionyl chloride to yield as the final product, n-butyl 4-[4-(6-chloro-2-quinolinyloxy)phenoxy]-3-oxopentanoate.

By using 2-[4-(6-fluoro-2-quinolinyloxy)phenoxy]-propionyl chloride as the starting material and ethyl alcohol in place of n-butyl alcohol in the process of Example 20, there is obtained ethyl 4-[4-(6-fluoro-2-quinlinyloxy) phenoxy]-3-oxopentanoate which is reduced using NaBH₄ in alcohol to yield ethyl 4-[4-(6-fluoro-2-quinolinyloxy) phenoxy]-3-hydroxypentanoate.

EXAMPLE 30

The compound, 6-fluoro-2-(4-hydroxyphenoxy) quinoxaline, is used as the starting material in Example 1 in place of 4-(2-chloro-4-trifluoromethylphenoxy)phenol to yield ethyl 4-[4-(6-fluoro-2-quinoxalyloxy)phenoxy]-3-methoxy-2-pentenoate which is reacted with aqueous perchloric acid by the process of Example 3 to yield ethyl 4-[4-(6-fluoro-2-quinoxalyloxy)phenoxy]-3-oxopentanoate. The 3-oxo ester on reduction with NaBH₄ yield the 4-hydroxy ester, ethyl 4-[4-(6-fluoro-2-quinoxalyloxy)phenoxy]-3-hydroxypentanoate.

What is claimed is:

1. A compound of the formula

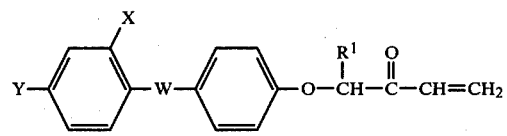

wherein W is oxygen, R¹ is hydrogen or lower alkyl and each of X and Y is independently selected from hydrogen, bromo, chloro, fluoro, lower alkyl, lower alkoxy, lower alkoxycarbonyl, nitro, cyano, trifluoromethyl, chlorodifluoromethyl, fluoromethyl, chloromethyl and difluoromethoxy.

2. A compound according to claim 1 wherein R¹ is methyl and X is hydrogen, chloro or nitro and Y is trifluoromethyl or chloro.

3. A compound according to claim 2 wherein X is hydrogen or chloro.

4. The compound, 4-[4-(4-trifluoromethyl phenoxy)-phenoxy]-3-oxo-1-pentene, according to claim 1.

5. The compound, 4-[4-(2-chloro-4-trifluoromethylphenoxy)phenoxy]-3-oxo-1-pentene, according to claim 1.

* * * * *

UNITED STATES PATENT AND TRADEMARK OFFICE
CERTIFICATE OF CORRECTION

PATENT NO. : 4,408,076

DATED : October 4, 1983

INVENTOR(S) : Shy-Fuh Lee

It is certified that error appears in the above-identified patent and that said Letters Patent is hereby corrected as shown below:

In Column 1, at line 40, after the word "wherein" please insert the phrase - - - R is - - -.

Signed and Sealed this

Twenty-sixth Day of March 1985

[SEAL]

Attest:

DONALD J. QUIGG

Attesting Officer

Acting Commissioner of Patents and Trademarks